United States Patent [19]

Fox et al.

[11] Patent Number: 5,540,033

[45] Date of Patent: Jul. 30, 1996

[54] INTEGRATED MANUFACTURING PROCESS FOR HYDROGELS

[75] Inventors: Adrian S. Fox, New Windsor; Joseph R. Flicek, New York; Barry J. Hand, Monroe, all of N.Y.

[73] Assignee: Cambrex Hydrogels, Harriman, N.Y.

[21] Appl. No.: 178,692

[22] Filed: Jan. 10, 1994

[51] Int. Cl.[6] ............................................. B65B 55/02
[52] U.S. Cl. ............................ 53/425; 424/412; 424/413; 424/414; 522/47
[58] Field of Search ................................. 424/412, 413, 424/414; 522/47; 53/425

[56] References Cited

U.S. PATENT DOCUMENTS

| | | | |
|---|---|---|---|
| 3,065,770 | 11/1962 | Svaty et al. | 139/127 |
| 3,264,202 | 8/1966 | King | 204/159.14 |
| 3,357,930 | 12/1967 | Marks | 252/518 |
| 3,419,006 | 12/1968 | King | 604/290 |
| 3,822,238 | 7/1974 | Blair et al. | 260/75 NK |
| 3,898,143 | 8/1975 | Assarsson et al. | 204/159.12 |
| 3,900,378 | 8/1975 | Yen et al. | 204/159.14 |
| 3,911,906 | 10/1975 | Reinhold | 128/2.06 E |
| 3,992,552 | 11/1976 | Assarsson et al. | 204/159.12 |
| 3,993,049 | 11/1976 | Kater | 128/641 |
| 3,993,551 | 11/1976 | Assarsson et al. | 204/159.14 |
| 3,993,552 | 11/1976 | King | 204/159.14 |
| 3,993,553 | 11/1976 | King | 204/159.14 |
| 3,994,302 | 11/1976 | Brennen | 128/404 |
| 3,998,215 | 12/1976 | Anderson et al. | 128/2.06 E |
| 4,008,721 | 2/1977 | Burton | 128/418 |
| 4,054,714 | 10/1977 | Mastrangela | 428/328 |
| 4,066,078 | 1/1978 | Berg | 128/2.06 |
| 4,067,342 | 7/1978 | Burton | 128/418 |
| 4,092,985 | 6/1978 | Kaufman | 128/303.13 |
| 4,094,822 | 6/1978 | Kater | 252/578 X |
| 4,109,648 | 8/1978 | Larke et al. | 128/2.06 E |
| 4,125,110 | 11/1978 | Hymes | 128/2.06 E |
| 4,141,366 | 2/1979 | Cross, Jr. et al. | 128/418 |
| 4,156,066 | 5/1979 | Gould | 528/73 |
| 4,156,067 | 5/1979 | Gould | 528/73 |
| 4,192,827 | 3/1980 | Mueller et al. | 525/123 |
| 4,273,135 | 6/1981 | Larimore et al. | 128/640 |
| 4,274,420 | 6/1981 | Hymes | 128/641 |
| 4,300,575 | 11/1981 | Wilson | 128/798 |
| 4,317,278 | 3/1982 | Carmon et al. | 29/878 |
| 4,318,746 | 3/1982 | Claffey et al. | 106/194 |
| 4,362,165 | 12/1982 | Carmon et al. | 128/640 |
| 4,365,634 | 12/1982 | Bare et al. | 128/640 |
| 4,383,529 | 5/1983 | Webster | 128/802 X |
| 4,393,584 | 7/1983 | Bare et al. | 29/877 |
| 4,458,696 | 7/1984 | Larimore | 128/798 |
| 4,474,570 | 10/1984 | Ariura et al. | 604/20 |
| 4,515,162 | 5/1985 | Yamamoto et al. | 128/640 |
| 4,522,211 | 6/1985 | Bare et al. | 128/640 |
| 4,522,223 | 6/1985 | Balsy et al. | 137/240 |
| 4,524,087 | 6/1985 | Engel | 427/2 |
| 4,539,996 | 9/1985 | Engel | 128/640 |
| 4,543,958 | 10/1985 | Cartmell | 128/640 |
| 4,554,924 | 11/1985 | Engel | 128/640 |
| 4,593,053 | 6/1986 | Jevne et al. | 523/111 |
| 4,684,558 | 8/1987 | Keusch et al. | 428/40 |
| 4,706,680 | 11/1987 | Keusch et al. | 128/640 |
| 4,750,482 | 6/1988 | Sieverding | 128/156 |
| 4,777,954 | 10/1988 | Keusch et al. | 128/640 |
| 4,813,210 | 3/1989 | Masuda et al. | 53/425 |
| 4,860,754 | 8/1989 | Sharik et al. | 128/640 |
| 4,983,181 | 1/1991 | Civerchia | 128/640 |
| 4,989,607 | 2/1991 | Keusch et al. | 128/640 |
| 5,143,071 | 9/1992 | Keusch et al. | 128/640 |
| 5,354,790 | 10/1994 | Keusch et al. | 523/300 |
| 5,392,590 | 2/1995 | Ambrose et al. | 53/425 |

FOREIGN PATENT DOCUMENTS

| | | | |
|---|---|---|---|
| 0107376 | 5/1984 | European Pat. Off. | 128/639 |
| WO9414657 | 7/1994 | WIPO | 53/425 |

*Primary Examiner*—Thurman K. Page
*Assistant Examiner*—Peter F. Kulkosky
*Attorney, Agent, or Firm*—Pennie & Edmonds

[57] ABSTRACT

A method for producing a sterile packaged adhesive hydrogel product by preparing an aqueous mixture of water, a polymer which can be cross-linked by radiation to form a hydrogel, and a cross-linking inhibitor in an amount sufficient to retard the cross-linking of the polymer when the mixture is exposed to radiation; providing the mixture in a predetermined shape or configuration representative of a hydrogel product; enclosing the shaped mixture in a sealed package; and subjecting the package to a dose of radiation sufficient to simultaneously cross-link and sterilize the mixture to provide a sterile packaged adhesive hydrogel product. The invention also is directed to the sterile packaged adhesive hydrogel product formed by this method, as well as the packaged product prior to sterilization. These products include one of the aqueous mixtures described above in a predetermined shape or configuration representative of a reinforced or non-reinforced hydrogel product and a sealed package enclosing the shaped mixture.

18 Claims, No Drawings

INTEGRATED MANUFACTURING PROCESS FOR HYDROGELS

TECHNICAL FIELD

This invention relates to a vertically integrated process for manufacturing sterilized packages of adhesive, cross-linked hydrogel materials, as well as to the hydrogel products which are made by the process.

BACKGROUND OF THE INVENTION

The art has employed various aqueous solutions of polymeric materials which can be gelled by radiation to form hydrogels. U.S. Pat. No. 5,143,071 lists a number of such hydrogels and specifically discloses polyvinyl pyrrolidone and polyethylene oxide hydrogels formed from aqueous solutions which are cross-linked by radiation dosages of 0.5 to 4.5 Mrads.

The prior art also shows sterile adhesive gel-foil packages made by a process that entails forming an aqueous polymer mixture into a hydrogel, subjecting the hydrogel to radiation to form a partially cross-linked hydrogel; forming the cross-linked hydrogel into sheets; applying a foil to each side of the cross-linked hydrogel to provide a package, and subjecting the resulting package to radiation to sterilize the hydrogel. Although the method of prior art produces sterile adhesive, hydrogel packaged product, the numerous steps required generates considerable processing expense.

A need therefore exists for methods which overcome the disadvantages of the prior art while providing a hydrogel packaged product that has acceptable properties and sterility.

SUMMARY OF THE INVENTION

The invention relates to a method for producing a sterile packaged adhesive hydrogel product comprising the steps of preparing an aqueous mixture of water, a polymer which can be cross-linked by radiation to form a hydrogel, and a cross-linking inhibitor in an amount sufficient to retard the cross-linking of the polymer when the mixture is exposed to radiation; providing the mixture in a predetermined shape or configuration representative of a hydrogel product; enclosing the shaped mixture in a sealed package; and subjecting the package to a dose of radiation sufficient to simultaneously cross-link and sterilize the mixture to provide a sterile packaged adhesive hydrogel product.

The providing step advantageously comprises casting the mixture onto a substrate in the desired shape and at a thickness of between about 20 and 100 mils. The reinforced mixtures may be cast to a thickness of between about 25 and 80 mils. The shape may be in the form of a sheet or series of discrete areas or regions of mixture. If desired, the mixture may be reinforced prior to being enclosed in the package. One type of reinforcement is achieved by providing a scrim material in contact with the cast mixture prior to enclosing it in the package.

In one aspect of the invention, the substrate forms a portion of the package. Alternatively, a liner material may be utilized as the substrate and the liner material and mixture are enclosed together in the sealed package. A separate cover material can be secured onto the substrate to form a sealed package about the mixture. Preferably, the substrate and cover material are made of a radiation resistant thermoplastic or a metal foil which does not block radiation so that the mixture can be cured and sterilized by the radiation.

Although any cross-linkable polymer can be used, preferred polymers include polyethylene oxide, polyvinyl pyrrolidone or mixtures thereof. These polymers are typically present in an amount of about 3 to 35 wt % of the mixture.

The cross-linking inhibitor is preferably a food grade antioxidant, such as ascorbic acid, an ester of ascorbic acid, an amide of ascorbic acid, sorbic acid, 3,4-dihydroxy-L-phenylalanine, hydroquinine, mono-ascorbate, di-ascorbate, or sorbate.

The dosage of radiation is effective to cause the mixture to have an adhesive face in which a rolling ball tack test gives a rolling ball distance of about 10 mm and 30 mm, and an adhesion energy force in the Adhesion Energy Density Determination Test of about 7 to 60 g-cm/cm$^2$. Also, to cross-link the polymer and sterilize the package, high energy electrons are applied to the package for a time sufficient to generate an applied dose to the mixture of at least about 2.7 Mrad but an absorbed dose in the mixture of between about 0.5 to 2.5 Mrad.

The sterile packaged adhesive hydrogel product formed by this method represents yet another aspect of the invention. Yet another embodiment is the product prior to sterilization. This product includes one of the aqueous mixtures described above in a predetermined shape or configuration representative of a reinforced or non-reinforced hydrogel product and a sealed package enclosing the shaped mixture. Thus, the package may be subjected to a dose of radiation sufficient to simultaneously cross-link and sterilize the mixture to provide a sterile packaged adhesive hydrogel product.

Having briefly summarized the invention, the invention will now be described in detail by reference to the following specification and non-limiting examples. Unless otherwise specified, all percentages are by weight and all temperatures are in degrees Celsius.

DETAILED DESCRIPTION OF THE INVENTION

In forming the aqueous polymer mixtures useful in the invention, the polymer(s), cross-linking inhibitor(s), and water are combined to provide a mixture. Slow agitation in a device such as a low shear type mixer or in a continuous extruder for about 1–24 hours is employed to provide these mixtures. The amount of cross-linking inhibitor is sufficient to prevent substantially complete cross-linking of the polymer by radiation dosages which are otherwise sufficient to sterilize the resulting hydrogel. The amount of cross-linking inhibitor, however, is not so high as to prohibit gelling of the polymer to provide an adhesive hydrogel. Generally, the amount of cross-linking inhibitor will be at least about 100 ppm and can vary from between about 500 to 1000 ppm (0.05 to 0.1%). Higher or lower amounts may be used depending upon the particular formulation. Specific amounts of cross-linking inhibitors can be determined by those skilled in the art by routine testing in accordance with the specific polymer and formulation employed and the dosage of radiation used.

Aqueous mixtures useful in the invention may be formed from any cross-linkable hydrophilic polymer. Typically, polymers such as polyethylene oxide ("PEO"), polyvinylpyrrolidone ("PVP"), and the like in weight percentages of about 3 to 35 percent, preferably about 4–20%, most preferably about 6–10%, may be employed. Other weight percentages of polymer may be employed depending on the polymers and amount of cross-linking inhibitor employed in the solution to be irradiated.

PEOs useful in the invention include linear, water soluble polyethylene oxides which have a weight average molecular weight ($M_w$) of 0.02–6×10$^6$ Daltons. A commercially available PEO polymer known as POLYOX (WRS N-205), having a $M_w$ of about 500 to 2000 Kilodaltons (kD) can be employed. A most preferred amount of PEO in the formulation is 7.5%.

The PVP is typically a polymer of N-vinyl-2-pyrrolidone having a $M_w$ of about 200 kD to about 2,000 kD. An advantageous polymer is PVP having a $M_w$ of about 1,000,000. Homogeneous aqueous mixtures comprising about 5 to about 35 weight percent of PVP are suitable to achieve the objects of the present invention. Preferred concentrations of PVP in the aqueous mixtures are about 10 to about 35 weight percent, most preferably 15 to 25 wt %. The irradiation cross-linking of PVP mixtures are most recently described in U.S. Pat. No. 4,699,146 issued to Sieverding, the disclosure of which is incorporated herein by reference.

To reduce the transverse electrical resistance of the homogeneous aqueous mixtures described herein and consequently, the hydrogels which are produced therefrom, a variety of electrolytic substances may be added to the mixtures in amounts sufficient to produce conductive products. These electrolytes may be ionizable inorganic salts, organic compounds, or combinations of both. Examples of such salts include, but are not limited to, ammonium sulfate, monoethanolamine acetate, diethanolamine acetate, sodium chloride, magnesium sulfate, calcium sulfate, ammonium acetate, magnesium chloride, magnesium acetate, or combinations thereof. Preferably, the electrolyte used is stable and inert upon dissolving in the aqueous mixture and the subsequent radiation cross-linking step. Preferred salts are potassium chloride, sodium chloride, magnesium sulfate, or magnesium acetate. Potassium chloride is most preferred for EKG applications. Although virtually any amount of electrolyte may be present in the mixture, a breakdown in viscosity is observed as discussed further below, and it is preferable to have an amount of water-soluble electrolyte present at a concentration of about 0.1 to about 15 wt % of the mixture. However, the amount of electrolyte present must be effective to reduce the transverse electrical resistance of the mixture, and the resulting hydrogel, to an impedance at 10 Hz–5 MHz of less than about 1,000 ohms. Typically, about 5 wt % of an electrolyte such as potassium chloride is sufficient to reduce the impedance at 60 HZ to much less than about 100 ohms.

Additional additives can be included in the present formulations. A humectant can be used to improve the physical properties of the hydrogels. The presence of humectant gives rise to a hydrogel that has a longer in-use lifetime than conventional hydrogels. This latter property is particularly desirable and advantageous because it allows longer uninterrupted medical or therapeutic treatment of an individual with fewer applications and replacement of wound dressings, electrodes, cosmetics, ultrasound coupling sheets, topical or transdermal drug delivery systems, protective drapes or other bodily contact hydrogel-based devices.

Examples of humectants that can be used in the present invention include but are not limited to glycerol, propylene glycol, poly-(ethylene glycol), N-methyl pyrrolidone, N-ethyl pyrrolidone, diacetone alcohol, γ-butyryl lactone, ethyl lactate, low molecular weight polyethylene glycol, or combinations thereof. Preferably, the humectant used in the present invention is biocompatible.

When humectants are used, it is advantageous to include a cross-linking promoter to assist in the cross-linking of the polymer. In addition, cross-linking promoters may be useful to help offset the effect of the cross-linking inhibitor. Examples of such cross-linking promoters that can be used in the present invention include but are not limited to N,N'-methylene-bis-acrylamide, ethylene glycol dimethacrylate or triethylene glycol dimethacrylate. Of course, optimum amounts of cross-linking inhibitors, humectants, cross-linking promoters, or other additives can be routinely determined for any particular formulation or composition.

Aqueous mixtures of polymer and cross-linking inhibitor can be cast onto a liner/foil such as the surface of an electrode, the surface of a wound dressing, or the surface of a band aid. A scrim typically is applied to the cast mixture when the thickness of the cast mixture is greater than about 25–30 mils. A low area-density scrim such as non-woven polyethylene can be immersed into the cast mixture prior to irradiating to provide increased strength to the resulting hydrogel. Other materials can be used for the scrim in particular applications. Reinforcing materials such as films, release liners, foils, fibers, mats, cloth or the like can be used, if desired.

After the aqueous polymer mixture is cast to the desired thickness and, if necessary, reinforced, it is subjected to high energy irradiation, such as a high energy electron flux as produced by an electron accelerator or Van De Graaf generator. In general, however, alpha particles, beta particles, gamma rays, X-rays, electron beams, or high energy ultraviolet radiation may be used to initiate or precipitate cross-linking of the polymer chains. The radiation has sufficient energy to completely penetrate the mixture so that the mixture receives a radiation dose effective to cross-link and sterilize the entire cross section of the cast mixture. Proper dose/energy/thickness relationships are readily available to those skilled in the art of radiation processing and therefore need not be discussed herein in detail. Typically, however, to achieve cross-linking effective to convert the viscous polymer/cross-linking inhibitor/optional additives/water mixture into a viscoelastic adhesive hydrogel, radiation doses typically of about 0.5 Mrads to about 4–5 Mrads, usually about 0.5 to about 2 Mrads are employed depending upon the selected polymer, its concentration, the cross-linking inhibitor and its concentration, as well as the presence of additional additives or functional, therapeutic agents.

Cross-linking inhibitors useful in the invention retard cross-linking of the polymers by absorbed doses of radiation of about 0.2 to 5 Mrads which are known in the art to yield sterile hydrogels, but can also yield a cross-linked hydrogel of little or no adhesiveness. Useful cross-linking inhibitors include antioxidant compounds, particularly food grade antioxidants such as ascorbic acid, BHA and BHT, and preferably ascorbic acid. It is believed that these inhibitors interrupt crosslinking by interrupting both the initiation phase by reducing the formation of free radicals and the propagation phase by inhibiting propagation from continuing.

The hydrogels produced in accordance with the invention are sterile and adhesive. Sterility can be confirmed, as is known in the art, by photochromic indicators such as those from Far West Technologies, Inc., Goleta, Calif., which are calibrated to National Institute of Science and Technology standards. The cross-linked hydrogels retain substantial adhesiveness, thereby making them suitable for use, for example, as electrodes for TENS (Transcutaneous Electrical Nerve Stimulation), ESU (Electro-surgical Unit), and EKG (electrocardiogram) applications.

The adhesiveness of the sterile, gelled polymer products of the invention is sufficient to provide in the rolling ball tack test a rolling ball distance of less than about 10–30 mm while yielding an adhesion energy force in the Adhesion Energy Force ("AED") Determination Test of at-least about 7 g-cm/cm$^2$, swell ratios of at least about 5, and percent gels of at least about 80. The adhesive strength of the gelled polymer product also is less than its cohesive strength. These properties enable the gelled polymer to be removed from a surface to which it is affixed without leaving a visible residue.

When a hydrogel package is ready for use as, for example, an electrode, the backing material is peeled from the package and the exposed surface of the hydrogel is applied to the skin of the patient. An electrode lead wire can be attached to the electrode at the fastener conductive member, as shown, for example, in U.S. Pat. No. 4,706,680, the content of which is expressly incorporated herein by reference thereto. Alternatively, the electrode can be provided with a lead wire already attached. The same sequence of foil removal and application of the electrode to the skin would then apply without the necessity of attaching a lead wire to the electrode before or during application.

The sterile hydrogel component of the packages of the invention have high adhesive strengths which enables them readily to be affixed to the skin and with little risk of accidentally dropping off through loss of adhesion. Because the hydrogel is water based, it is relatively immune to the effects of moisture on the skin and will not slide Off as a result of perspiration forming under the electrode while affixed to the skin. The sterile hydrogels also have high cohesive strengths, which means that they can be removed from the skin after use without leaving visible residue. Interestingly, although the hydrogels have a high adhesive strength, it is not high enough to pull hairs from the skin or irritate the skin when the hydrogel is removed therefrom.

If desired, non-stringy hydrogels can be prepared as disclosed in U.S. Pat. Nos. 4,989,607 or 5,143,071, the content of each of which is expressly incorporated herein by reference thereto.

Because the sterile hydrogels may lose water eventually under ambient conditions, they are preferably stored in a water and gas impermeable container, e.g., a polyfoil packet formed from the laminated plastic conventionally used to store measured amounts of freeze-dried or ground coffee. Sealed envelopes are conventionally produced by heat sealing a pair of sheets of thin plastic around the hydrogel sheet-backing laminate, or by heat sealing the open end of an otherwise sealed packet or envelope formed from a single sheet of the laminate.

If both faces of the hydrogel are covered with a release liner or foil, optionally different liners can be employed, one of which is more readily removable from the hydrogel than the other, e.g., a sheet of polyethylene covering one face and a sheet of "Mylar" plastic covering the other, thereby ensuring that a predetermined face of the film or sheet is exposed first- In some end use applications, one of the faces of the film or sheet can be covered with a conductive liner or foil which is not removable and is used as a conductive member. Other variations will be evident to those skilled in the art.

In another embodiment, a large sheet of a laminate formed from the hydrogel and films of plastic covering its faces, e.g., a film of polyethylene on one face and a film of Mylar on the other, is scored at spaced intervals to produce a plurality of severable units, each for individual use. This scoring can be done either before or after the hydrogel is polymerized and sterilized.

If desired, a plurality of shaped units such as circles, squares or rectangles of the hydrogel with a release liner covering one face of the hydrogel can be "stacked" one upon the other so that a column of units of the hydrogel sheet with both faces covered with a liner or foil is formed. Desirably, in such an arrangement, one side of the release liner has a higher adhesive value than the other, so that only one unit of the hydrogel is removed at a time from the column. Such columns can be conveniently stored in glass jars or aluminum lined paper tube with a moisture impervious cap which form a gas and moisture impervious sealed container. Again, this arrangement can be achieved before the hydrogel is polymerized and sterilized.

As stated above, the hydrogels employed in this invention are characterized by sterility, surface adhesiveness, and sufficient cohesiveness to maintain structural integrity when being removed from the skin.

To test for skin adhesiveness, samples of the hydrogel with backing removed from one side can be applied to the skin and left thereon. This can be done both with scrim-containing hydrogels films per se and with scrim-containing hydrogel film attached to a support backing that bears a metal conductive snap electrical terminal. The extent which the hydrogel adheres to the skin is observed and the ease by which the hydrogel can be separated from the skin is noted, along with whether or not any residue is left on the skin.

The adhesiveness and tackiness of the conductive hydrogel sheet or films can be quantified by the "Tack Rolling Ball Method" (TRAM) as specified by the Pressure Sensitive Tape Council. This test method for adhesive materials is detailed in The American Society for Testing Materials, Designation D3121-73 (Re-approved 1979) which test method is under the jurisdiction of ASTM Committee D-14 on Adhesives. The test utilizes an inclined trough which can be obtained through the Pressure Sensitive Tape Council, 1201 Waakegan Road, Glenview, Ill. 60025, that is equipped with a release lever at the top through which a 16.5 mm diameter, 21.7 g steel ball is released into the trough. The ball gains momentum as it descends the incline and rolls onto the adhesive surface whose adhesiveness is being measured, the shorter distance the ball travels thereon, the higher the adhesion value.

The test is performed as follows: Remove the backing materials from both sides of a hydrogel sample cut one inch wide and at least three inches long. The test is run in a controlled environment (72° F.±5° F. and 50%±10% relative humidity). A hard, horizontal surface of sufficient size to conduct the test is selected. Both metal and glass plates have proved satisfactory. Before testing each adhesive sheet, clean the inclined trough thoroughly with isopropanol.

The specimen to be tested is placed flat, adhesive side up, in line with the inclined trough. The end of the specimen opposite the incline is held to the table. Only one test is run on each specimen. Each time before the O ball is rolled onto the hydrogel, it is thoroughly cleaned with distilled water, isopropanol, or another appropriate solvent, which removes any residue that might otherwise remain from a previous test, and then wiped with a lint-free, bleached, absorbent material to remove any remaining residue. After cleaning the ball or raceway is not touched. Clean, dry tongs are used to place the ball on the upper side of the release. Release the ball and it will roll to a stop on the adhesive material. Measure the distance from the point where the ball initially contacts the adhesive to where the ball stops. The average of the stopping distance measurements of five or more tests is recorded. Pertinent additional comments based on visual inspection such as noticeable residue on ball, lift of adhesive from substrate, etc. are noted.

In this test, the hydrogels produced in accordance with the invention typically have tack rolling ball distances of at least about 10 mm, preferably 10–30 mm.

The extraction test may be used to measure the extent of cross-linking in a polymeric mixture involves an extraction test. This test provides % gel values and is carried out substantially as described below. A two inch by two inch piece of PVP hydrogel and weighing about 2.5 grams is extracted with 200 mL of distilled water for 72 hours at ambient temperature. The excess water is then removed from the swollen sheet which is then weighed. The swollen sheet is then baked in a 50° C. oven for 24 hours. The resulting desiccated hydrogel is then weighed. The ratio of the "dried" hydrogel weight over the original weight of the polymer in the sample is the gel fraction or % gel. Preferred hydrogels of the present invention have % gel values of at least about 80 percent.

An important feature for sterile, adhesive hydrogels such as those of the invention, especially for use in wound management applications, is the hydrogel's absorptive capacity. This property is important because a hydrogel, when placed on the skin, can readily lose its adhesive bond due to perspiration at the skin-gel interface. Moreover, if sterile hydrogel is utilized as a wound dressing, it must be capable of absorbing the exudate from the wound. If the hydrogel cannot do so, it will also lose its adhesive bond and move from the site where it was intended to function. For these reasons it is important for the sterile adhesive hydrogel to have good equilibrium or absorption capacity for aqueous liquids. A test method that quantitatively measures the absorption capacity of a cross-linked polymer system is the swelling test.

The swelling test method proceeds in the same manner as the extraction test previously mentioned, up to the point of extraction. The weight of the extracted sheet, with unbound excess water removed from the surface, is divided by the weight of the original sheet to yield the swell ratio (SR). The hydrogels of the present invention, may have an absorption capacity, as measured by the swell ratio (SR), of at least about 5.

Another test to measure strength of the adhesive bond of the hydrogel is the Adhesion Energy Density Determination test. This test measures how well a hydrogel sheet adheres to a flat surface. The Adhesion Energy which is measured represent the combined strength of the surface bond of hydrogel sheet to the flat surface and the strength of the hydrogel sheet itself (i.e., a combined cohesiveness/adhesiveness test.

In this test, a sample of the sterile hydrogel sheet is placed unbacked on a clean flat stainless steel block. The block in turn is placed on a block of flexible foam which in turn is placed on a test stand. With the setup in place a steel ring is placed on top of the test sample and aligned with the test probe to be used so that the latter will descend therethrough without touching the ring. A cylindrical (1.5 inch diameter) polymethylmethacrylate test probe then descends into the sample at a constant rate to a constant depth. (In the hydrogel films tested, the descent rate is set at 0.5 mm/sec. and the penetration is set at 1.0 mm.) Before the test probe is caused to descend, it is cleaned with isopropanol or distilled water and dried with a lint-free cloth to make certain no residual adhesive material is on the face of the probe before the test is begun. All tests are run at 72° F.±5° F. and at a relative humidity of 50%±10% and each test sample is stored at these conditions for at least one hour before the test. When the test probe has made its 1 mm descent into the hydrogel film and begins its return (at a rate of ascent of 0.344 cm/sec), the adhesive sample being tested has adhered to the face of the test probe.

From the start of the return of the probe to complete separation of the test sample from the face of the probe, the force on the probe and the corresponding displacement is recorded using a Voland Stevens LFRA Texture Analyzer and Recorder (Voland Corporation, Hawthorne, N.Y.). The area under the force-displacement curve is the adhesion energy. For the 1.5 inch diameter probe used it is the adhesion energy per 11.4 $cm^2$ which is the adhesion energy density. For the work reported herein, the force was measured in grams and the displacement measured in centimeters so that all adhesion energy densities are reported in $g-cm/cm^2$.

In this test, the hydrogels of this invention display adhesion energy densities of about 5 to about 60 $g-cm/cm^2$. The preferred hydrogels give values of at least about 7 $g-cm/cm^2$ in this test. Also, in this test, the hydrogels of the invention exhibit a force, equivalent to the height of the force-displacement curve, of at least about 180 grams. Preferably, the hydrogels of the present invention exert a force on the test probe equivalent to at least about 250 grams, most preferably 400 grams. In addition, the force-displacement curves obtained for the present hydrogels are sharp and substantially featureless.

If desired, and as mentioned previously, the hydrogels of this invention optionally can contain various additives. Possible additives include but are not limited to those mentioned above as well as preservatives, antifungal agents, bacteriostats and the like, bearing in mind that the additives selected must be able to withstand the irradiation employed to produce the sterile adhesive hydrogel. Such additives may be included in formulations at levels of about 3% or less. Presence of these additives can change the radiation doses required to give a sterile adhesive hydrogel. Addition of these additions therefore may require a shift upward in the radiation dose to reach the same level of desired cross-linking. However, shifts to lower levels are not necessarily precluded, and the optimum radiation dosages can easily be determined by routine testing.

The sterile adhesive hydrogels of the invention contain no extraneous or other objectional ingredients. All ingredients have proven bioacceptability on contact with the skin. Normal exudants flow into the matrix of the hydrogels away from the user's skin. The hydrogel's hydrophilic properties eliminate the common requirement for abrasive treatment and/or other skin preparation. The biocompatibility of the sterile hydrogels is expected to be quite favorable because all the ingredients used to prepare the hydrogels are themselves, highly biocompatible.

The sterile hydrogels of the invention do not contain free water. The water in the hydrogel is an integral part of the hydrogel structure and therefore cannot be separated therefrom by physical means such as pressure. Thus, the cross-linked matrix remains homogeneous under gravity and even at temperatures approaching freezing water.

The sterile, adhesive hydrogels and packages produced by the invention are a homogeneous aqueous mixture of water and cross-linked polymers. Known methods can be employed to determine the rate of crosslinking of the hydrogel as a function of absorbed radiation dosage to provide a gel-dose curve. The point on the gel-dose curve where a hydrogel is first formed is called the gelation dose. Immediately thereafter, the fraction of gel increases sharply as more of the polymer chains become part of the cross-linked network. Eventually the gel fraction reaches a plateau where no more cross-linking takes place. This is a routine exercise for determining the proper radiation dosage for curing the composition, and in the present invention consideration must also be made to assure that the composition is sterilized.

EXAMPLES

The invention will now be described in further detail by reference to the following, non-limiting examples.

Examples 1–7

Solutions containing polyethylene oxide, steam distilled water, preservatives and ascorbic acid (USP Grade) are prepared by mixing at ambient temperature. The specific amounts and percentages of these components are given in Table I.

TABLE I

| Ex. | PEO[1] N1105 grams (wt-%) | Water grams (wt-%) | Nipasept ™ Sodium[2] grams (wt-%) | Nipabutyl ™ Sodium[3] grams (wt-%) | Ascorbic Acid grams (wt-%) |
|---|---|---|---|---|---|
| 1 | 60 (6) | 937.2 (93.72) | 2.6 (0.26) | 0.12 (0.012) | — |
| 2 | 60 (6) | 937.15 (93.715) | 2.6 (0.26) | 0.12 (0.012) | 0.05 (0.005) |
| 3 | 60 (6) | 937.1 (93.71) | 2.6 (0.26) | 0.12 (0.012) | 0.10 (0.01) |
| 4 | 60 (6) | 936.95 (93.615) | 2.6 (0.26) | 0.12 (0.012) | 0.25 (0.025) |
| 5 | 60 (6) | 936.7 (93.67) | 2.6 (0.26) | 0.12 (0.012) | 0.50 (0.05) |
| 6 | 60 (6) | 936.45 (93.645) | 2.6 (0.26) | 0.12 (0.012) | 0.75 (0.075) |
| 7 | 60 (6) | 936.2 (93.62) | 2.6 (0.26) | 0.12 (0.012) | 1.00 (0.1) |

[1]Polyox N1105, Union Carbide Corp.
[2]Nipasept ™ Sodium preservative, Nipa Laboratories, Inc., contains less than 70% methyl paraben, sodium salt, more than 15% ethyl paraben, sodium salt, and more than 10% propyl paraben, sodium salt.
[3]Nipabutyl ™ Sodium preservative, Nipa Laboratories, Inc., Butyl Paraben, sodium salt.

Each of the mixtures of Examples 1–7 of Table I is coated by a doctor blade onto a 3-mil low density polyethylene (LDPE) sheet to provide 50–60 mil thickness films. Each of the cast films is covered with a polyethylene non-woven scrim that has an area-density of 0.016 g/in$^2$. A three mil LDPE sheet is applied over the scrim to provide packages.

The packages are irradiated with a 1.5 MeV Van der Graaf electron accelerator at 0.9 milliamps beam current while transported on a conveyer at 3.5 meters/minute to produce an absorbed dose of 2.5 Mrads. The adhesiveness and area densities of the resulting sterile, adhesive hydrogels in the gel-foil packages are shown in Table II.

TABLE II

| EXAMPLE | AREA DENSITY (G./FT$^2$) | TRBM(1)* (MM) | REMARKS |
|---|---|---|---|
| 1 | 132 | >50 | No surface tack. Rubber-like |
| 2 | 130 | >50 | No surface tack. |
| 3 | 135 | >50 | No surface tack. |
| 4 | 130 | >50 | No surface tack. |
| 5 | 133 | 48 | Very slightly tacky. |
| 6 | 130 | 40 | Very slightly tacky. |
| 7 | 131 | 32 | Slightly tacky. |

*TRBM(1) is Tack Rolling Ball Method as per PSTC (Pressure Sensitive Tape Council) Test Method # 6 using a 11.1 mm, 5.6 g., stainless steel ball.

Examples 8–10

Three samples of the mixtures employed in Example 7 are doctor bladed onto 3 mil LDPE sheets to provide a 50–60 mil thickness films. Each of the films is covered with a non-woven polyethylene scrim of an area density of 0.016 g/in$^2$ and a 1 mil LDPE sheet as described in Examples 1–7 to provide packages. The package of example is irradiated with a 1.5-MeV Van der Graaf electron accelerator operating at 0.9 milliamps while moving at 3.5 m/m line speed to produce an absorbed dose of 3.4 Mrads. Similarly, the packages of examples 9 and 10, while moving at 3.5 m/m line speed, are irradiated by the accelerator operating at 0.67 milliamps and at 0.45 milliamps to produce absorbed doses of 2.4 Mrads and 1.7 Mrads respectively. The area densities and adhesiveness of the resulting sterile hydrogels in the gel-foil packages are shown in Table III.

TABLE III

| EXAMPLE | ABSORBED DOSE (Mrads) | AREA DENSITY (G./FT$^2$) | TRBM(1)* (MM) |
|---|---|---|---|
| 8 | 3.4 | 133 | >50 |
| 9 | 2.4 | 132 | 32 |
| 10 | 1.7 | 132 | 15 |

*TRBM(1) is Tack Rolling Ball Method as per PSTC (Pressure Sensitive Tape Council) Test Method # 6 using a 11.1 mm, 5.6 g., stainless steel ball.

Examples 11–25

Three molecular weight grades of Polyethylene oxide (Polyox™-Union Carbide Corp.), water, and ascorbic acid are formulated as shown in Table IV. These formulations are formed into packages as in Examples 1–7 and treated with radiation from the 1.5 Mev Van der Graaf electron accelerator to provide absorbed doses of 0.5–2.5 Mrad. The adhesiveness of the resulting hydrogels in the gel-foil packages is shown in Table IV.

TABLE IV

| EXAMPLE | PEO | ASCORBIC ACID CONC., PPM | WATER | SOLUTION VISCOSITY CPS ("C" Spindle, 20 rpm) | pH[4] | ABSORBED DOSE, Mrads | TRBM (1)* (MM) |
|---|---|---|---|---|---|---|---|
| 11 | 4%[1] | — | Remainder | 40,000 | 8.3 | 0.5 | 30 |
| 12 | 4%[1] | 500 | Remainder | 10,000 | 6.9 | 1.0 | 13 |
| 13 | 4%[1] | 500 | Remainder | 10,000 | 6.9 | 2.0 | 53 |
| 14 | 4%[1] | 750 | Remainder | 7,000 | 6.4 | 1.5 | 20 |
| 15 | 4%[1] | 750 | Remainder | 7,000 | 6.4 | 2.5 | 25 |
| 16 | 7%[2] | — | Remainder | 16,000 | 8.2 | 1.0 | 39 |
| 17 | 7%[2] | 500 | Remainder | 14,000 | 7.0 | 1.0 | 7 |
| 18 | 7%[2] | 500 | Remainder | 14,000 | 7.0 | 2.0 | 20 |
| 19 | 7%[2] | 750 | Remainder | 13,000 | 6.3 | 1.5 | 18 |
| 20 | 7%[2] | 750 | Remainder | 13,000 | 6.3 | 2.0 | 19 |
| 21 | 7%[3] | — | Remainder | 25,000 | 8.3 | 1.0 | 57 |
| 22 | 7%[3] | 500 | Remainder | 22,000 | 7.2 | 1.5 | 22 |
| 23 | 7%[3] | 500 | Remainder | 22,000 | 7.2 | 2.5 | 53 |
| 24 | 7%[3] | 750 | Remainder | 21,000 | 7.1 | 1.0 | 16 |

TABLE IV-continued

| EXAMPLE | PEO | ASCORBIC ACID CONC., PPM | WATER | SOLUTION VISCOSITY CPS ("C" Spindle, 20 rpm) | pH[4] | ABSORBED DOSE, Mrads | TRBM (1)* (MM) |
|---|---|---|---|---|---|---|---|
| 25 | 7%[3] | 750 | Remainder | 21,000 | 7.1 | 2.0 | 20 |

*TRBM(1) is Tack Rolling Ball Method as per PSTC (Pressure Sensitive Tape Council) Test Method # 6 using a 11.1 mm, 5.6 g., stainless steel ball.
[1]POLYOX PEO 301 from Union Carbide
[2]POLYOX PEO 205 from Union Carbide
[3]POLYOX PEO 1105 from Union Carbide
[4]pH of mixture prior to irradiation Examples 26–31

Compositions are blended from poly-(vinyl pyrrolidone) and poly-(ethylene oxide) which contain various levels of ascorbic acid using the procedure of Example 1. The compositions are shown in Table V.

TABLE V

| EX. | PVP K90[1] [g. (wt-%)] | PEO 1105[2] [g. (wt-%)] | WATER [g. (wt-%)] | PHENONIP ™ * [g. (wt-%)] | ASCORBIC ACID (USP) [g. (wt-%)] |
|---|---|---|---|---|---|
| 26 | 200 (20) | 10 (1) | 787.0 (78.7) | 3 (0.3) | — |
| 27 | 200 (20) | 10 (1) | 786.99 (78.699) | 3 (0.3) | 0.01 (0.001) |
| 28 | 200 (20) | 10 (1) | 786.95 (78.695) | 3 (0.3) | 0.05 (0.005) |
| 29 | 200 (20) | 10 (1) | 786.9 (78.69) | 3 (0.3) | 0.1 (0.01) |
| 30 | 200 (20) | 10 (1) | 786.5 (78.65) | 3 (0.3) | 0.5 (0.05) |
| 31 | 200 (20) | 10 (1) | 786 (78.6) | 3 (0.3) | 1 (0.1) |

*Phenonip ™, Nipa Laboratories, Inc., contains >70% 2 phenoxyethanol, >15% methyl paraben, <5% ethyl paraben, <5% propyl paraben and <10% butyl paraben.
[1]PVP K90 from BASF Corp.
[2]Polyox N1105 from Union Carbide Corp.

Each of the mixtures in Examples 26–31 is doctor bladed onto a 3-mil LDPE sheet to provide films of 50–60 mils thickness. Each of the films is covered with a polyethylene non-woven scrim (0,016 g/in$^2$ area density) and a one mil LDPE sheet to provide packages. The packages are irradiated with a 1.5 MeV van der Graaf electron accelerator at 0.9 milliamps beam current while moving at 4 meters/minute conveyer line speed to produce an absorbed dose of 2.9 Mrads to generate sterile, adhesive gel-foil packages. The results are shown in Table VI.

TABLE VI

| EXAMPLE | AREA DENSITY (G./FT$^2$) | TRBM(1)* (MM) | REMARKS |
|---|---|---|---|
| 26 | 132 | >50 | No surface tack. Rubber-like |
| 27 | 130 | 30 | No surface tack. |
| 28 | 135 | 27 | No surface tack. |
| 29 | 130 | 31 | No surface tack. |
| 30 | 133 | 21 | Good surface tack. |
| 31 | 130 | 12 | Very good surface tack. |

*TRBM(1) is Tack Rolling Ball Method as per PSTC (Pressure Sensitive Tape Council) Test Method # 6 using 6.5 mm, 21.7 g., stainless steel ball.

Examples 32–38

Solutions containing polyethylene oxide, steam distilled water, preservatives and ascorbic acid (USP Grade) are prepared by mixing at ambient temperature. The specific amounts and percentages of these components are given in Table VII.

Each of the mixtures of Examples 32–38 of Table VII is coated by a doctor blade onto a 3-mil low density polyethylene (LDPE) sheet to provide 50–60 mil thickness films. Each of the cast films is covered with a polyethylene non-woven scrim that has an area density of 0,016 g/in$^2$.

Each of the cast films is irradiated with a 1.5 MeV Van der Graaf electron accelerator at 0.9 milliamps beam current while transported on a conveyer at 3.5 meters/minute to produce an absorbed dose of 2.5 Mrads.

TABLE VII

| Ex. | PEO[1] N1105 grams (wt-%) | Water grams (wt-%) | Nipasept ™ Sodium[2] grams (wt-%) | Nipabutyl ™ Sodium[3] grams (wt-%) | Ascorbic Acid grams (wt-%) |
|---|---|---|---|---|---|
| 32 | 60 (6) | 937.2 (93.72) | 2.6 (0.26) | 0.12 (0.012) | — |
| 33 | 60 (6) | 937.15 (93.715) | 2.6 (0.26) | 0.12 (0.012) | 0.05 (0.005) |
| 34 | 60 (6) | 937.1 (93.71) | 2.6 (0.26) | 0.12 (0.012) | 0.1 (0.01) |
| 35 | 60 (6) | 936.95 (93.615) | 2.6 (0.26) | 0.12 (0.012) | 0.25 (0.025) |
| 36 | 60 (6) | 936.7 (93.67) | 2.6 (0.26) | 0.12 (0.012) | 0.5 (0.05) |
| 37 | 60 (6) | 936.45 (93.645) | 2.6 (0.26) | 0.12 (0.012) | 0.75 (0.075) |
| 38 | 60 (6) | 936.2 | 2.6 (0.26) | 0.12 (0.012) | 1 |

TABLE VII-continued

| Ex. | PEO[1] N1105 grams (wt-%) | Water grams (wt-%) | Nipasept ™ Sodium[2] grams (wt-%) | Nipabutyl ™ Sodium[3] grams (wt-%) | Ascorbic Acid grams (wt-%) |
|---|---|---|---|---|---|
| | (6) | (93.62) | (0.26) | (0.012) | (0.1) |

[1]Polyox N1105, Union Carbide Corp.
[2]Nipasept ™ Sodium preservative, Nipa Laboratories, Inc., contains less than 70% methyl paraben, sodium salt, more than 15% ethyl paraben, sodium salt, and more than 10% propyl paraben, sodium salt.
[3]Nipabutyl ™ Sodium preservative, Nipa Laboratories, Inc., Butyl Paraben, sodium salt.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for producing a sterile packaged adhesive hydrogel product comprising the steps of:

preparing an aqueous mixture of water, a water soluble, high molecular weight polymer which can be cross-linked by radiation to form a hydrogel, and a cross-linking inhibitor in an amount sufficient to retard the cross-linking of the polymer when the mixture is exposed to radiation;

providing the mixture in a predetermined shape or configuration representative of a hydrogel product;

enclosing the shaped mixture in a sealed package; and subjecting the package to a dose of radiation sufficient to simultaneously cross-link and sterilize the mixture to provide a sterile packaged hydrogel product having sufficient tack as measured by the Tack Rolling Ball Method to be useful as an adhesive, wherein said tack is sufficiently improved over the same product which is irradiated without the cross-linking inhibitor.

2. The method of claim 1 wherein the providing step comprises casting the mixture onto a substrate in the desired shape and at a thickness of between about 20 and 100 mils.

3. The method of claim 2 wherein the providing step further comprises casting the mixture on the substrate in the form of a sheet.

4. The method of claim 2 wherein the providing step further comprises casting the mixture on the substrate in the form of a series of discrete areas.

5. The method of claim 1 which further comprises reinforcing the mixture prior to enclosing it in the package.

6. The method of claim 2 which further comprises reinforcing the cast mixture by providing a scrim material in contact with the cast mixture prior to enclosing it in the package.

7. The method of claim 6 which further comprises casting the mixture to a thickness of greater than 25 mils.

8. The method of claim 2 which further comprises utilizing a liner material as the substrate and enclosing the liner material and mixture in the sealed package.

9. The method of claim 2 wherein the enclosing step comprises securing a cover material onto the substrate to form the sealed package.

10. The method of claim 9 which further comprises selecting the substrate and cover material to be a radiation resistant thermoplastic or a metal foil which does not block radiation.

11. The method of claim 1 which further comprises selecting the polymer to be a polyethylene oxide, polyvinylpyrrolidone or mixture thereof.

12. The method of claim 11 which further comprises selecting the polymer to be polyethylene oxide and providing the polymer in an amount of about 5 to 35 wt % of said mixture.

13. The method of claim 11 which further comprises selecting the polymer to be polyvinylpyrrolidone and providing the polymer in an amount of about 5 to 35 wt % of said mixture.

14. The method of claim 11 which further comprises selecting the polymer to include both polyethylene oxide and polyvinylpyrrolidone and providing the polymers in a total amount of about 5 to 5 wt % of said mixture.

15. The method of claim 1 which further comprises selecting the cross-linking inhibitor to be a food grade antioxidant.

16. The method of claim 1 which further comprises selecting the cross-linking inhibitor to ascorbic acid, an ester of ascorbic acid, an amide of ascorbic acid, sorbic acid, 3,4-dihydroxy-L-phenylalanine, hydroquinine, mono-ascorbate, di-ascorbate, or sorbate.

17. The method of claim 1 wherein the dosage of radiation is effective to cause the mixture to have an adhesive face in which a rolling ball tack test gives a rolling ball distance of about 10 mm and 30 mm, and an adhesion energy force in the Adhesion Energy Density Determination Test of about 7 to 60 g-cm/cm$^2$.

18. The method of claim 1 wherein the subjecting step comprises applying high energy electrons to the package for a time sufficient to generate an applied dose to the mixture of at least about 2.7 Mrad but an absorbed dose in the mixture of between about 0.5 to 2.5 Mrad so that the mixture is polymerized while the package is sterilized.

* * * * *